United States Patent [19]
Torii et al.
[11] 4,237,308
[45] Dec. 2, 1980

[54] PROCESS FOR PREPARING 2-CYCLOPENTENONE DERIVATIVE AND PERFUME COMPOSITION CONTAINING THE DERIVATIVE

[75] Inventors: Sigeru Torii; Hideo Tanaka; Yuichi Kobayashi, all of Okayama, Japan

[73] Assignee: Otsuka Kagaku Yakuhin Kabushiki Kaisha, Japan

[21] Appl. No.: 913,691

[22] Filed: Jun. 8, 1978

[30] Foreign Application Priority Data

Aug. 12, 1977 [JP] Japan ................................. 52-97173

[51] Int. Cl.[3] ........................................... C07C 67/738
[52] U.S. Cl. ................................ 560/122; 252/522 R
[58] Field of Search ......................................... 560/122

[56] References Cited

U.S. PATENT DOCUMENTS

| | | | |
|---|---|---|---|
| 3,836,581 | 9/1974 | Bernady et al. | 260/560 |
| 3,954,834 | 5/1976 | Cohen | 260/468 |
| 3,959,263 | 5/1976 | Abraham et al. | 260/240 |
| 4,007,216 | 2/1977 | McFearin | 260/468 |
| 4,014,919 | 3/1977 | Johnson | 260/468 |

OTHER PUBLICATIONS

Bindra, et al., Prostaglandin Synthesis, p. 342 (1977).
House, Modern Synthetic Reactions, pp. 514–515 (1972).
Mitre, The Synthesis of Prostaglandins, pp. 186, 401 (1977).
Parfums, Cosmetiques, aromes 12, pp. 53–60 (1976).

*Primary Examiner*—Robert Gerstl
*Attorney, Agent, or Firm*—Armstrong, Nikaido, Marmelstein & Kubovcik

[57] ABSTRACT

A process for preparing 2-cyclopentenone derivative represented by the formula

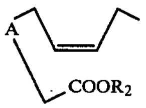

wherein A is

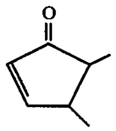
or

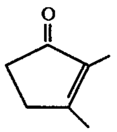

, and $R_2$ is lower straight-chain or branched-chain alkyl, alkenyl or aralkyl, and perfume composition containing the derivative.

1 Claim, No Drawings

PROCESS FOR PREPARING 2-CYCLOPENTENONE DERIVATIVE AND PERFUME COMPOSITION CONTAINING THE DERIVATIVE

This invention relates to a process for preparing 2-cyclopentenone derivatives and perfume compositions containing the derivative.

The 2-cyclopentenone derivatives produced by the process of this invention are represented by the formula

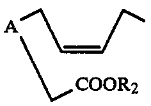

(1)

wherein A is

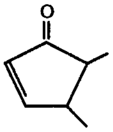

or

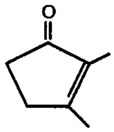

, and $R_2$ is lower straight-chain or branched-chain alkyl, alkenyl or aralkyl. The compounds (1), although not occurring in natural jasmine oil, have a unique jasmine-like fragrance and are useful as novel perfumes similar to jasmine.

According to this invention, the compounds (1) are prepared by decarboxylating, for example, 5-(cis-2-pentenyl)-2-cyclopentenone derivative represented by the formula

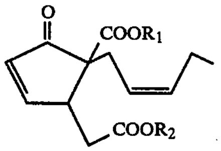

(2)

wherein $R_1$ is lower branched-chain alkyl, and $R_2$ is lower straight-chain or branched-chain alkyl, alkenyl or aralkyl.

Furthermore, 2-(cis-2-pentenyl) cyclopentanone derivatives useful as main fragrant components of jasmine oil and represented by the formula

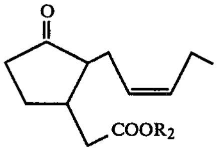

wherein $R_2$ is as defined above can be obtained from the compounds (1) of this invention in exceedingly higher yields than conventionally possible. This process is represented by the following equation:

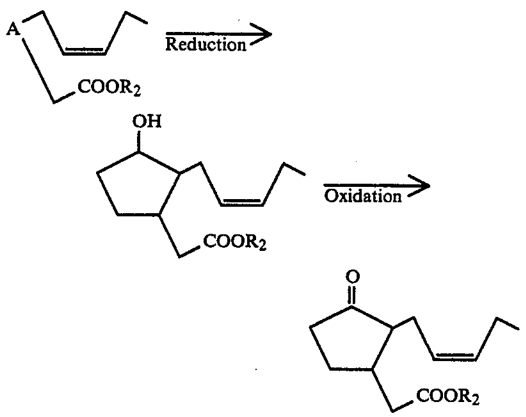

(1)

(3)

(4)

It is known to prepare the compound (4), for example, by the process reported by G. Buchi and B. Egger in J. Org. Chem. 36, 2021 (1971). This process is represented as follows:

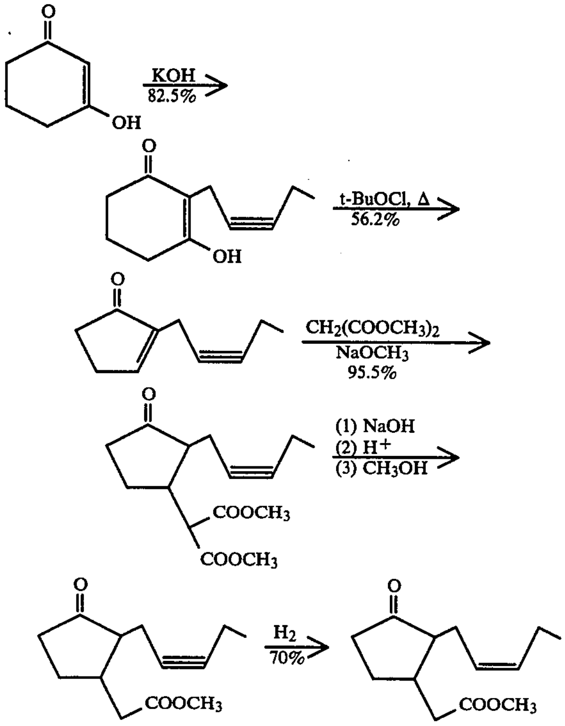

The known process illustrated above gives an overall yield of as low as up to 30% even if assuming that the methoxycarbonyl removing step achieves a yield of 100%. Since the starting material is not easily available, this process, when using a more readily available starting material, would involve an increased number of steps and result in a further reduced yield. Many other processes, although reported, achieve similar or lower yields, require a special reagent or a reagent which is hazardous or likely to cause pollution and involve a complex reaction procedure.

The compound (2) which is used as the starting material of this invention is novel and prepared for example by the following process.

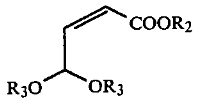

+ $CH_3COCH_2COOR_1$ (5) (6)

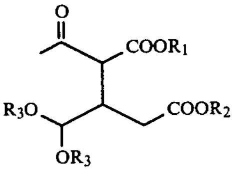

(7)

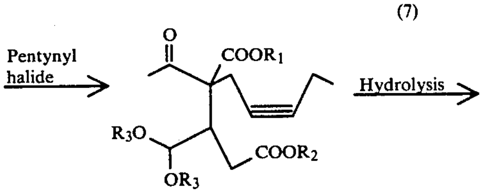

(8)

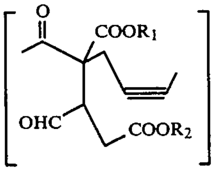

(9)

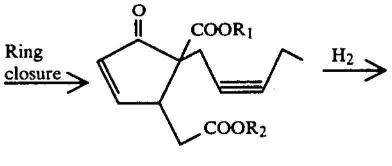

(10)

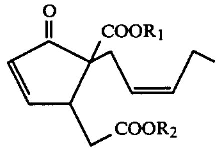

(2)

The group $R_1$ in the foregoing formulae is lower branched-chain alkyl. Examples of useful alkyl groups are iso-propyl, iso-butyl, sec-butyl, tert-butyl, iso-pentyl, iso-hexyl, sec-hexyl, etc.

The groups $R_2$ and $R_3$ are each lower straight-chain or branched-chain alkyl, alkenyl or aralkyl. Examples of groups $R_1$, $R_2$ and $R_3$ are alkyl groups such as methyl, ethyl, n-propyl, iso-propyl, n-butyl, sec-butyl, n-pentyl, neo-pentyl, n-hexyl, iso-hexyl, etc.; alkenyl groups such as vinyl, allyl, 1-propenyl, butenyl, pentenyl, hexenyl, etc; and aralkyl groups such as benzyl, phenetyl, methyl-benzyl, phenylpropyl, etc.

The compound (5) is a cis-2-butenate derivative which is easily prepared for example by electrolytically oxidizing furfuryl alcohol. The compound (8) is obtained by subjecting the derivative and an acetoacetate (6) to condensation to prepare a compound (7) and reacting the compound (7) with pentynyl halide. The compound (8) gives a compound (10) when subjected to ring closure directly or after hydrolysis. The compound (2), the starting material of this invention, is obtained by reducing the compound (10).

The compounds (1) of this invention can be prepared by the decarboxylation of compounds (2). The reaction conditions, when suitably selected, give a compound (1) which consists singly of a compound of the formula (1-a) given below or which comprises a mixture of a compound of the formula (1-a) and a compound of the formula (1-b) below.

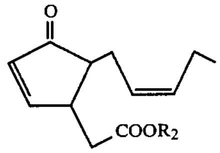

(1-a)

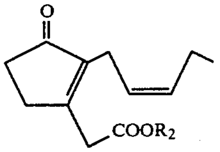

(1-b)

The compound (1-a) alone can be obtained by decarboxylating the compound (2) in the presence of a catalyst with use of an inert solvent. Examples of useful catalysts are sulfonic acids such as p-toluenesulfonic acid, benzenesulfonic acid; mineral acids such as hydrochloric acid and sulfuric acid; organic acids such as formic acid and acetic acid; Lewis acids such as boron trifluoride, aluminum chloride and zinc chloride. Examples of useful solvents are aromatic hydrocarbons such as benzene and toluene; aliphatic ethers such as tetrahydrofuran, dioxane and ethyl ether; aliphatic hydrocarbons such as n-hexane and n-heptane; hydrocarbon halides such as dichloromethane and dichloroethane; and mixtures of such solvents. The reaction temperature which is not particularly limited, is usually 40° to 120° C., preferably 60° to 100° C.

The mixture of compound (1-a) and compound (1-b) can be obtained by reacting the compound (2) in a solvent such as dimethylformamide or dimethyl sulfoxide with use of sodium chloride as a catalyst, whereby the carboxylate at the 5th position only can be removed, with transfer of the double bond also taking place. The reaction temperature, although not particularly limited, is usally 100° to 200° C., preferably 130° to 180° C.

The reduction of the compound (1) to the compound (3) is conducted advantageously in the presence of a solvent and a reducing agent. Examples of useful solvents are water, alcohols such as methanol and ethanol, aliphatic ethers such as tetrahydrofuran, dioxane and ethyl ether, dimethylformamide, dimethyl sulfoxide and like polar solvents, and mixtures of such solvents. Examples of useful reducing agents are lithium aluminum hydride, lithium trialkoxyaluminum hydride, diisopropylaluminum hydride and like aluminum hydrides, and sodium borohydride, potassium borohydride and like borohydrides. The reducing agent is used preferably in an amount of about 2 to about 6 moles per mole of the compound (1). The reaction temperature is usually 0° to 150° C., preferably 20° to 80° C.

The oxidation of the compound (3) to the compound (4) is conducted advantageously in the presence of a solvent and an oxidizing agent. Examples of useful solvents are inert solvents including hydrocarbon halides such as dichloromethane and dichloroethane; aliphatic ethers such as tetrahydrofuran, dioxane and ethyl ether; aliphatic hydrocarbons such as n-hexane and n-heptane; and aromatic hydrocarbons such as benzene and toluene. Examples of useful oxidizing agents are a chromic acid-sulfuric acid combination, (Jones' reagent), $KMnO_4$, potassium bichromate, lead tetraacetate, lead oxide, peroxide and nitric acid. The oxidizing agent is used in an amount of about 0.5 to about 3 moles, preferably about 1 to about 1.5 moles, per mole of the compound (3). The reaction temperature, which is not particularly limited, is usually −20° to 50° C., preferably 5° to 30° C.

The process described above affords the compounds (1), (3) and (4) according to this invention. The compounds (1), (3) and (4), although available individually from isolated starting materials, can be produced with use of an unisolated reaction mixture as the starting material. The compounds obtained can be easily purified in the usual manner as by extraction, distillation, chromatography and recrystallization.

This invention will be described below with reference to Examples and Reference Examples.

REFERENCE EXAMPLE 1

Into a 500-ml reactor are placed 40 g of potassium fluoride, 40 ml of dry tert-butanol, 123 g of methyl cis-4,4-dimethoxy-2-butenate and 36 g of tert-butyl acetoacetate. The mixture is heated at 100° C. with stirring on an oil bath for two days. On completion of the reaction, the tert-butanol is distilled off from the mixture. The residue is dissolved in ethyl acetate, and the solution washed with an aqueous solution of common salt and then dried. The solvent is removed from the product. The resulting residue is purified by a silica gel column and distilled at reduced pressure, giving methyl 4-tert-butoxycarbonyl-3-dimethoxymethyl-5-oxohexanoate (compound (7), $R_1$=t-Bu, $R_2$=$R_3$=$CH_3$) in a yield of 95.4%, b.p. 72°–76° C./0.014 mm Hg.

| Elementary analysis: | C | H |
|---|---|---|
| Found (%) | 56.65 | 8.13 |
| Calculated (%) | 56.59 | 8.23 |

IR: 2851 $cm^{-1}$ ($CH_3O$), 1736 $cm^{-1}$ (C=O), 1715 $cm^{-1}$ (C=O).

NMR ($CCl_4$): 1.43 (bs 9, $CH_3$), 3.19–3.38 (m 6, $CH_3O$), 3.58–3.72 (m 3, $CH_3OCO$), 3.19–3.72 (m 1, CH), 4.31 (t 1, 5 Hz, OCHO).

REFERENCE EXAMPLE 2

A 1.38 g quantity of potassium carbonate and 308 mg of potassium iodide are placed into a reactor. Acetone (30 ml) and a solution of 450 mg of methyl 4-tert-butoxycarbonyl-3-dimethoxymethyl-5-oxohexanoate in 10 ml of acetone are further placed into the reactor. Subsequently 270 mg of pentynyl bromide is added to the mixture. The resulting mixture is stirred at room temperature for one hour and thereafter refluxed at 70° C. for 13 hours. On completion of the reaction, the mixture is cooled to room temperature, and the solids are separated off. The product is concentrated in a vacuum, and the residue purified by a silica gel column, giving methyl 4-acetyl-4-tert-butoxycarbonyl-3-dimethoxymethyl-6-nonynoate (compound (8), $R_1$=t-Bu, $R_2$=$R_3$=$CH_3$) in a yield of 91%.

-continued

| Elementary analysis: | C | H |
|---|---|---|
| Found (%) | 62.54 | 8.35 |
| Calculated (%) | 62.50 | 8.39 |

IR: 2837 $cm^{-1}$ ($CH_3O$), 1729 $cm^{-1}$ (>C=O), 1710 $cm^{-1}$ (>C=O), 1430 $cm^{-1}$ ($CH_2$), 1354 $cm^{-1}$ ($CH_3O$).

NMR ($CCl_4$) (δ value): 1.11 (3 H, $CH_3$—C); 2.26–2.55 (2 H, $CH_2COO$); 2.55–2.85 (2H, $CH_2$—C≡); 3.61, 3.65 (6H, $CH_3OCO$); 4.18–4.39

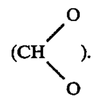

REFERENCE EXAMPLE 3

Methyl 4-acetyl-4-tert-butoxycarbonyl-3-dimethoxymethyl-6-nonynoate (546 mg) is dissolved in 30 ml of tetrahydrofuran, and 25 ml of 1.5% aqueous solution of perchloric acid is added to the solution. The mixture is stirred at 28° C. for 12 hours. Subsequently the reaction mixture is neutralized with sodium bicarbonate and concentrated in a vacuum. The residue is extracted with ethyl acetate. The extract is dried and then concentrated to give methyl 4-acetyl-4-tert-butoxycarbonyl-3-formyl-6-nonynoate (compound (9), $R_1$=t-Bu, $R_2$=$CH_3$) in a yield of 98.0%.

NMR ($CCl_4$): 9.65 (CHO).

IR (neat): 2841 $cm^{-1}$ (CHO), 1733, 1716 $cm^{-1}$ (>C=O),

A 790 mg quantity of the compound (9) obtained above is dissolved in 50 ml of benzene containing 1 ml of acetic acid and 1 ml of piperidine, and the solution is refluxed for 4 hours. On completion of the reaction, the solvent is removed, and the residue dissolved in ethyl acetate. The solution is washed with water and an aqueous solution of sodium bicarbonate and thereafter dried. The residue is distilled in a vacuum, giving 5-tert-butoxycarbonyl-4-methoxycarbonylmethyl-5-(2-pentynyl)-2-cyclopentenone (compound (10), $R_1$=t-Bu, $R_2$=$CH_3$) in a yield of 78%, b.p. 82°–86° C./0.006 mm Hg.

| Elementary analysis: | C | H |
|---|---|---|
| Found (%) | 67.36 | 7.70 |
| Calculated (%) | 67.48 | 7.55 |

NMR ($CCl_4$): 1.02 (t 3, $CH_3$), 1.37 (bs 9, $CH_3$), 1.76–2.73 (m. 6, $CH_2C$=C, $CH_2CO$), 3.33–3.58 (m. 1, CH), 3.66 (s 3, $CH_3O$), 6.10 (dd. 1, 5 Hz, 2 Hz, C=CHCO), 7.50 (dd. 1, 5 Hz, 2 Hz, HC=CCO).

REFERENCE EXAMPLE 4

A 690 mg quantity of 5-tert-butoxycarbonyl-4-methoxycarbonylmethyl-5-(2-pentynyl)-2-cyclopentenone (compound (10)) is dissolved in a mixture of 5 ml of n-hexane and 5 ml of acetone and reduced at room temperature and atmospheric pressure with addition of 3.2 g of a Lindlar catalyst. The catalyst is filtered off from the reaction mixture, and the solvent distilled off. The residue is purified by a silica gel column and distilled in a vacuum, giving 5-tert-butoxycarbonyl-4-methoxycarbonylmethyl-5-(cis-2-pentenyl)-2-cyclopentenone (compound (2), $R_1$=t-Bu, $R_2=CH_3$) in a yield of 99.8%, b.p. 81°-84° C./0.005 mm Hg.

| Elementary analysis: | C | H |
|---|---|---|
| Found (%) | 66.91 | 8.36 |
| Calculated (%) | 67.06 | 8.13 |

NMR ($CCl_4$): 0.97 (t. 3, $CH_3$), 1.42 (s. 9, $CH_3$), 2.05 (q, 7 Hz, 2, $CH_2C=C$), 2.34-2.71 (m. 4, $CH_2C=C$, $CH_2CO_2$), 3.26 (m. 1, 9 Hz, CH), 3.66 (s. 3, $CH_3O$), 4.79-5.69 (m. 2, CH=CH), 6.09 (dd. 1, 5 Hz, 2 Hz, C=CHCO), 7.50 (dd. 1, 5 Hz, 2 Hz, HC=CCO).

EXAMPLE 1

A 540 mg quantity of 5-tert-butoxycarbonyl-4-methoxycarbonylmethyl-5-(cis-2-pentenyl)-2-cyclopentenone and 10 mg of p-toluene sulfonic acid are dissolved in 20 ml of benzene, and the solution is refluxed for 20 minutes. The resulting reaction mixture is neutralized with sodium bicarbonate. The solvent is distilled off from the mixture, and the residue is distilled in a vacuum, giving 4-methoxycarbonylmethyl-5-(cis-2-pentenyl)-2-cyclopentenone (compound (1-a), $R_2=CH_3$) in a yield of 91%, b.p. 88°-92° C./2.5 mm Hg.

| Elementary analysis: | C | H |
|---|---|---|
| Found (%) | 70.06 | 8.19 |
| Calculated (%) | 70.24 | 8.16 |

NMR ($CDCl_3$): 0.95 (t. 3, $CH_3$), 1.88-3.18 (m. 8), 3.70 (s. 3, $CH_3O$), 4.95-5.75 (m. 2, CH=CH), 6.15 (dd. 1, 6 Hz, 1.6 Hz, C=CHCO), 7.60 (dd, 6 Hz, 2 Hz, HC=CCO).

EXAMPLE 2

A 360 mg quantity of 5-methoxycarbonyl-4-methoxycarbonylmethyl-5-(cis-2-pentenyl)-2-cyclopentenone is dissolved in 8 ml of dimethyl sulfoxide containing 23 mg of water. The solution is reacted in a sealed tube with addition of 20 mg of sodium chloride. After the solution has been heated at 175° C. for 4 hours, the product is cooled to room temperature and then extracted with ethyl ether. The ethereal layer is washed, dried and distilled for the removal of the solvent. Purification of the residue by a silica gel column affords a compound (1-a) and compound (1-b) ($R_2=CH_3$ in each). Yield of compound (1-a): 62.5%. Yield of compound (1-b): 28.5%. Combined yield: 91%. B.p. 87°-91° C./2.5 mm Hg.

Compound (1-a)

| Elementary analysis: | C | H |
|---|---|---|
| Found (%) | 70.26 | 8.17 |
| Calculated (%) | 70.24 | 8.19 |

IR: 1596 $cm^{-1}$ (C=C).

NMR ($CCl_4$): 3.64 ($CH_3OCO$), 6.04, 7.46 (ring—HC=CH).

Compound (1-b)

| Elementary analysis: | C | H |
|---|---|---|
| Found (%) | 70.21 | 8.20 |
| Calculated (%) | 70.24 | 8.19 |

IR: 1643 $cm^{-1}$ (C=C).

NMR ($CCl_4$): 3.63 ($CH_3OCO$).

REFERENCE EXAMPLE 5

A 180 mg quantity of 4-methoxycarbonylmethyl-5-(cis-2-pentenyl)-2-cyclopentenone and 90 mg of sodium borohydride are dissolved in 20 ml of methanol, and the solution is refluxed at 80° C. for one hour. The reaction mixture is thereafter cooled to room temperature, and 20 ml of acetic acid is added to the mixture. The resulting mixture is stirred for 30 minutes and then concentrated at reduced pressure. The concentrate is distilled in a vacuum, giving 3-methoxycarbonylmethyl-2-(cis-2-pentenyl)-cyclopentanol (compound (3), $R_2=CH_3$) in a yield of 94%, b.p. 63°-67° C./0.01 mm Hg.

| Elementary analysis: | C | H |
|---|---|---|
| Found (%) | 69.00 | 9.75 |
| Calculated (%) | 68.99 | 9.80 |

NMR ($CCl_4$): 0.99 (t. 3, $CH_3$), 1.22-2.88 (m. 13), 3.61 (s. 3, $CH_3O$), 3.67-4.22 (m. 1, CHO), 5.20-5.52 (m. 2, HC=CH).

REFERENCE EXAMPLE 6

A 150 mg quantity of 3-methoxycarbonylmethyl-2-(cis-2-pentenyl)-cyclopentanol is dissolved in 10 ml of methylene chloride. A 2 ml quantity of chromic acid solution of 2 M concentration is added dropwise to the solution. The mixture is stirred at about 18° C. for 12 hours and thereafter extracted with ethyl acetate. The extract is washed with aqueous solution of sodium chloride, dried and concentrated. The residue is purified with a silica gel column and distilled in a vacuum, affording 3-methoxycarbonylmethyl-2-(cis-2-pentenyl)-cyclopentanone (compound (4), $R_2=CH_3$) in a yield of 88%, b.p. 92°-96° C./2.7 mm Hg.

IR: 1742 $cm^{-1}$ (C=O).

NMR ($CDCl_3$): 0.95 (t. 3, $CH_3$), 1.40-2.90 (m. 12), 3.68 (s. 3, $CH_3O$), 5.35 (m. 2, HC=CH).

EXAMPLE 3

The following compounds are mixed together in the proportions given below to prepare a perfume composition.

| | |
|---|---|
| Phenethyl alcohol | 12 wt. parts |
| Geraniol | 16 |
| Linalool | 6 |
| Eichenmoos absolute | 6 |
| Benzyl acetate | 9 |
| Amylcinnamaldehyde | 4 |
| 4-Methoxycarbonylmethyl-5-(cis-2-pentenyl)-2-cyclopentenone | 3 |
| Stearyl acetate | 2 |
| Vetiveryl acetate | 9 |
| Bergamot | 9 |
| Ilang-ilang oil | 3 |

-continued

| | |
|---|---|
| Neroli bigarade | 2 |
| methylionone | 9 |
| Indole | 2 |
| 1,1-Dimethyl-6-t-butyl-4-acetylindane | 1 |
| γ-undecylenic lactone | 2 |
| Rose oil | 1 |
| Jasmine oil | 2 |
| Undecyl aldehyde | 8 |
| Dodecyl aldehyde | 4 |
| | 100 wt. parts |

EXAMPLE 4

A perfume composition is prepared from the following components in the proportions given below.

| | |
|---|---|
| Benzyl acetate | 100 wt. parts |
| Phenethyl alcohol | 90 |
| Geraniol | 60 |
| Linalool | 40 |
| Bergamot | 90 |
| Ilang-ilang oil | 30 |
| Neroli bigarade | 15 |
| Amylcinnamaldehyde | 40 |
| α-Methyl-β-isopropylphenyl-propionaldehyde | 5 |
| Hydroxy citronellal | 240 |
| Methylionone | 120 |
| Vetiveryl acetate | 60 |
| 4-Ethoxycarbonylmethyl-5-(cis-2-pentenyl)-2-cyclopentenone | 20 |
| Methylisoeugenol | 20 |
| 1,1-Dimethyl-6-t-butyl-4-acetylindane | 10 |
| Burgarian rose oil | 20 |
| Jasmine oil | 40 |
| | 1000 wt. parts |

EXAMPLE 5

A perfume composition is prepared from the following components in the proportions given below.

| | |
|---|---|
| Bergamot | 7 wt. parts |
| Ilang | 4 |
| Hydroxy citronellal | 20 |
| Geraniol | 5 |
| Linalool | 4 |
| Phenethyl alcohol | 2 |
| Heliotropin | 4 |
| Methylionone | 6 |
| Benzyl acetate | 7 |

-continued

| | |
|---|---|
| Musk ketone | 10 |
| Jasmine absolute | 5 |
| 3-Methoxycarbonylmethyl-2-(cis-2-pentenyl)-2-cyclopentenone | 18 |
| Amylcinnamaldehyde | 5 |
| Rose absolute | 3 |
| | 100 wt. parts |

EXAMPLE 6

The following components are admixed with a base composition having a jasmine-like fragrance to prepare a fortified composition of the jasmine type.

| | |
|---|---|
| Hexylpentanone | 10 wt. parts |
| Amylcinnamaldehyde | 15 |
| Decyl acetate | 1 |
| 4-Methoxycarbonylmethyl-5-(cis-2-pentenyl)-2-cyclopentenone | 50 |
| 3-Ethoxycarbonylmethyl-2-(cis-2-pentenyl)-2-cyclopentenone | 24 |
| | 100 wt. parts |

These dehydrojasmonates have the properties of both jasminelactone and cis-jasmonate and impart a jasmine-like fragrance to perfume compositions or add to or fortify the fragrance of perfume compositions.

What is claimed is:

1. A process for preparing a mixture of 2-cyclopentenone derivatives represented by the formulae:

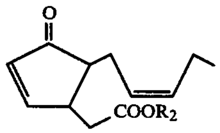
and
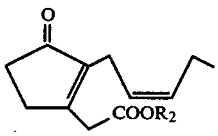

wherein $R_2$ is lower straight-chain or branched-chain alkyl, alkenyl or aralkyl, comprising decarboxylating 5-(cis-2-pentenyl)-2-cyclopentenone derivative represented by the formula:

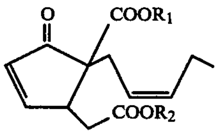

wherein $R_1$ is branched-chain alkyl, and $R_2$ is as defined above in the presence of sodium chloride.

* * * * *